United States Patent [19]

Los

[11] Patent Number: 5,110,930

[45] Date of Patent: May 5, 1992

[54] PROCESS FOR THE PREPERATION OF 2-(2-IMIDAZOLIN-2-YL) PYRIDINES AND QUINOLINES

[75] Inventor: Marinus Los, Pennington, N.J.

[73] Assignee: American Cyanamid Company, Stamford, Conn.

[21] Appl. No.: 686,633

[22] Filed: Apr. 17, 1991

Related U.S. Application Data

[60] Division of Ser. No. 484,754, Feb. 26, 1990, Pat. No. 5,021,078, which is a division of Ser. No. 280,906, Dec. 9, 1988, Pat. No. 4,923,504, which is a division of Ser. No. 850,192, Apr. 10, 1986, Pat. No. 4,798,619, which is a division of Ser. No. 382,041, May 25, 1982, Pat. No. 4,638,668, which is a continuation-in-part of Ser. No. 252,704, Apr. 8, 1981, abandoned, which is a continuation-in-part of Ser. No. 155,909, Jun. 2, 1980, abandoned, which is a continuation-in-part of Ser. No. 155,910, Jun. 2, 1980, abandoned, which is a continuation-in-part of Ser. No. 155,867, Jun. 2, 1980, abandoned, which is a continuation-in-part of Ser. No. 155,908, Jun. 2, 1980, abandoned, which is a continuation-in-part of Ser. No. 155,865, Jun. 2, 1980, abandoned.

[51] Int. Cl.$^5$ .............................................. C07D 401/04
[52] U.S. Cl. ...................................... 546/15; 546/112; 546/167; 546/183; 546/278
[58] Field of Search .................. 546/15, 112, 183, 167, 546/278

[56] References Cited

U.S. PATENT DOCUMENTS 4,155,578  9/1978  Miller et al. .................... 546/278

Primary Examiner—Bernard Dentz
Attorney, Agent, or Firm—John W. Hogan, Jr.

[57] ABSTRACT

There are provided novel 2-(2-imidazolin-2-yl)pyridine and quinoline compounds, a process and intermediate compounds for the preparation thereof, and a method for controlling a wide variety of annual and perennial plant species therewith.

2 Claims, No Drawings

PROCESS FOR THE PREPERATION OF 2-(2-IMIDAZOLIN-2-YL) PYRIDINES AND QUINOLINES

SUMMARY OF THE INVENTION

This is a divisional application of U.S. application Ser. No. 484,754 filed on Feb. 26, 1990, now U.S. Pat. No. 5,021,078 which is a divisional application of Ser. No. 07/280,906 filed Dec. 9, 1988, now U.S. Pat. No. 4,923,504 which is a divisional of Ser. No. 850,192 filed Apr. 10, 1986 which is now U.S. Pat. No. 4,798,619 (1989), which is a division of Ser. No. 382,041 filed May 25, 1982 which is now U.S. Pat. No. 4,638,068 (1987), which is a continuation-in-part of Ser. No. 252,704 filed Apr. 8, 1981, now abandoned, which is a continuation-in-part of abandoned applications Ser. Nos. 155,909, 155,910, 155,867, 155,908 and 155,865 all filed Jun. 2, 1980.

The invention is a process for the preparation of a compound having the structure of formula I

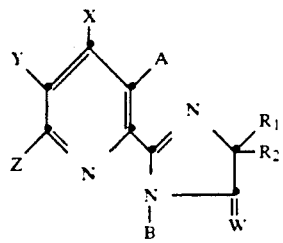

wherein
$R_1$ is $C_1$-$C_4$ alkyl;
$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;
A is $COOR_3$ or $CONHR_6$;
$R_3$ is
  $C_1$-$C_{12}$ alkyl optionally substituted with one of the following groups; $C_1$-$C_3$ alkoxy, halogen, hydroxyl, $C_3$-$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;
  $C_3$-$C_{12}$ alkenyl optionally substituted with one of the following groups: $C_1$-$C_3$ alkoxy, phenyl, halogen or loweralkoxycarbonyl or with two $C_1$-$C_3$ alkoxy groups or two halogen groups;
  $C_3$-$C_6$ cycloalkyl optionally substituted with one or two $C_1$-$C_3$ alkyl groups;
  $C_3$-$C_{10}$ alkynyl optionally substituted with one or two $C_1$-$C_3$ alkyl groups; or
  A cation of alkali metals, alkaline earth metals, manganese, copper, iron, zinc, cobalt, lead, silver, nickel, ammonium or organic ammonium;
$R_6$ is hydrogen, hydroxyl, $C_3$-alkenyl, $C_3$-alkynyl or $C_1$-$C_4$ alkyl optionally substituted with one hydroxyl or one chlorine group;
B is H;
W is O;
X is hydrogen, halogen, hydroxyl or methyl, with the proviso that when Y and Z are taken together to form a ring and YZ is represented by the structure: $-(CH_2)_n-$, where n is 3 or 4, X is hydrogen;
Y and Z are each hydrogen, halogen, $C_1$-$C_6$ alkyl, hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino or $C_1$-$C_4$ alkylsulfonyl group, or phenyl optionally substituted with one $C_1$-$C_4$ alkyl, $C_1$-$C_4$ alkoxy or halogen; and, when taken together, Y and Z may form a ring in which YZ are represented by the structure: $-(CH_2)_n-$, where n is an integer of 3 or 4, provided that X is hydrogen; or

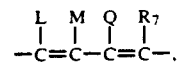

where L, M, Q and $R_7$ are each hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$ may represent a substituent other than hydrogen, halogen, $C_1$-$C_4$ alkyl or $C_1$-$C_4$ alkoxy; comprising; reacting a compound having the structure:

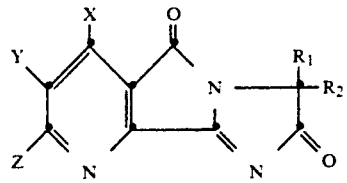

wherein $R_1$, $R_2$, X, Y and Z are as described above; with (a) at least one equivalent of an alcohol represented by the structure $R_3OH$ and an alkali metal alkoxide $R_3O^-M^+$, where $R_3$ is as described above and $M^+$ is an alkali metal, at a temperature between about 20° C. and 50° C., alone or in the presence of an aprotic solvent; whereby the desired product, in which A is $COOR_3$ and $R_3$, $R_1$, $R_2$, X, Y and Z are as described above, is formed; or with (b) at least one equivalent of an amine represented by the structure $R_6NH_2$, where $R_6$ is as described above, alone or in the presence of an aprotic solvent, at a temperature between about 80° C. and 125° C., whereby the desired product, in which A is $CONHR_6$ and $R_6$, $R_1$, $R_2$, X, Y and Z are as described above, is formed.

The invention is, further, a process for the preparation of compounds having the structure of formula I wherein B, W, X, Y, Z, $R_1$ and $R_2$ are as described hereinabove and A is $COOR_3$, $CONHR_6$, $CH_2OH$, $COCH_3$, $COC_6H_5$, or

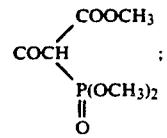

which comprises reacting a compound having the structure:

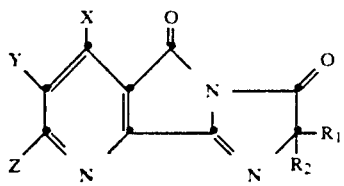

wherein $R_1$, $R_2$, X, Y and Z are as described above; with a) at least one equivalent of an alcohol represented by the structure $R_3OH$ and an alkali metal alkoxide $R_3O^{\ominus}M^+$, where $R_3$ is as described above and M is an alkali metal, alone or in the presence of an aprotic solvent at a temperature between 20° C. and 50° C., whereby the desired product, in which A is $COOR_3$ and $R_3$, $R_1$, $R_2$, X, Y and Z are as described above, is obtained;

b) at least one equivalent of an amine represented by the structure $R_6NH_2$, where $R_6$ is as described above, in the presence of a loweralkyl alcohol or an aprotic solvent at a temperature between about 80° C. and 125° C., whereby the desired product, in which A is $CONHR_6$ and $R_6$, $R_1$, $R_2$, X, Y and Z are as described above, is obtained;

c) at least one equivalent of methyl magnesium bromide, in the presence of an aprotic solvent at a temperature between −50° C. and −80° C. under a blanket of inert gas, whereby the desired product in which A is $COCH_3$ and $R_1$, $R_2$, X, Y and Z are as described above, is obtained;

d) at least one equivalent phenyl lithium, in the presence of an aprotic solvent at a temperature between −50° C. and −80° C. under a blanket of inert gas, whereby the desired product, in which A is $COC_6H_5$ and $R_1$, $R_2$, X, Y and Z are as described above, is obtained; or e) at least one equivalent of trimethylphosphonoacetate, in the presence of an aprotic solvent at −50° C. to −80° C. under a blanket of inert gas, whereby the desired product in which A is

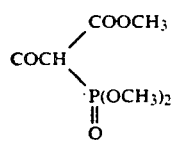

and $R_1$, $R_2$, X, Y and Z are as described above, is obtained; or f) at least one equivalent of sodium borohydride in ethanol at −10° to +20° C. whereby the desired product in which A is $CH_2OH$, is obtained.

Compounds having the structure of formula I and their herbicidal use are described in U.S. Pat. No. 4,798,619, issued on Jan. 17, 1989 and incorporated herein by reference thereto.

EXAMPLE 1

Preparation of 3-Isopropyl-3-methyl-5H-imidazo[1',2',:1,2]pyrrolo[3,4,6]pyridine-2-(3H), 5-dione A mixture of 50 g amide and 450 ml toluene is heated under a Dean-Stark water separator to remove traces of water. To the cooled mixture is added 10.1 g of a 50% suspension of sodium hydride in mineral oil and the mixture heated under reflux for 23 hours. The hot solution is filtered, concentrated in vacuo where upon the residue is crystallized. The mineral oil is removed by decantation and the solid washed with hexanes and dried in vacuo to give 45.5 g product which, by nmr analysis, is approximately 90% the desired isomer II and 10% the undesired isomer IIa.

A pure sample of isomer II can be obtained by recrystallizing the crude product from hexanemethylene chloride mp 107°–115° C.

The cyclisation can be achieved by either the basic reagent sodium and potassium hydroxide, or the acidic reagent p-toluenesulfonic acid in a toluene solvent. It should be understood that a mixture of products corresponding to Structures II and IIa above is obtained and in general these are not purified but used directly for the preparation of the derived nicotinic acid esters.

Employing the appropriate pyrrolopyridine carboxamide, the following imidazopyrrolopyridines are prepared.

| $R_1$ | $R_2$ | X | Y | Z | mp °C. |
|---|---|---|---|---|---|
| $CH_3$ | $CH_3$ | H | H | H | |
| $CH_3$ | $C_2H_5$ | H | H | H | |
| $CH_3$ | △ | H | H | H | |
| —CH—$CH_2CH_2CH_2$—<br>\|<br>$CH_3$ | | H | H | H | 125–130 |
| $CH_3$ | $CH(CH_3)_2$ | H | H | $OCH_3$ | 147–147.5 |

EXAMPLE 2

Preparation of 3-Isopropyl-5-H-imidazo[2',2':1,2]pyrrolo[3,4-6]pyridine-2(3H)-dione A mixture containing 52 g of 3-[(1-Carbamoyl-1,2-dimethylpropyl)picolinate], 1.77 ml 1,5-diazabicyclo[5.4.0]-undec-5-ene(DBU) in 400 ml xylene is heated under reflux under a Dean-Stark water separator for 2 hours. The mixture is concentrated in vacuo and the residue is chromatographed on 400 g basic alumina. The mixture of desired products is eluted with methylene chloride and used without further purification.

EXAMPLE 3

Preparation of Methyl 2-(isopropyl-5-methyl-4-oxo-2-imidazolin-2-yl)nicotinate

To 20 ml dry methanol in which 10 mg sodium hydride had reacted is added 2.0 g of a mixture of the imidazopyrrolopyridines. After stirring for 16 hours, 0.03 g glacial acetic acid is added (to neutralize the base), the solution concentrated in vacuo and the residue chromatographed on silica gel in ether. The faster moving material, the desired ester, is obtained in several fractions, combined, concentrated and crystallized from acetonitrile to give the imidazolinyl nicotinate, mp 121°-123.5° C. An analytically pure sample crystallized from methylene chloride hexane exhibits a melting point of from 121°-122° C.

EXAMPLE 4

Preparation of Methyl 2-(5-isopropyl-5-methyl-4-oxo-2-imidazolin-yl)nicotinate

This method involves the formation of the tricyclic compounds of Example 3 and 4, without isolation, directly forming the nicotinic acid esters:

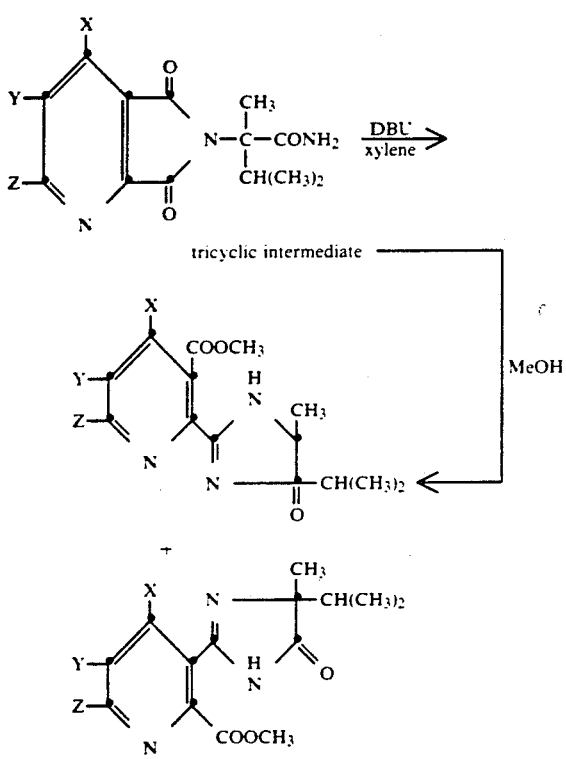

A mixture of 25 g amide and 1 ml 1,5-diaza-bicyclo-[5.4.0]undec-5-ene(DBU) in 500 ml xylene is heated under reflux for 1 hour under a Dean-Stark water separator. The mixture is cooled somewhat, the water separator removed, 100 ml anhydrous methanol added and the mixture heated under reflux for 1 hour. The solvents are then removed in vacuo and the product isolated by chromatography as described in Example 5 above to give 13.65 g product mp 120°-122° C. identical to that described in Example 5 above.

EXAMPLE 5

Preparation of 4[2-(5-Isopropyl-5-methyl-4-oxo-2-imidazolin-2-yl)nicotinoyl]morpholine

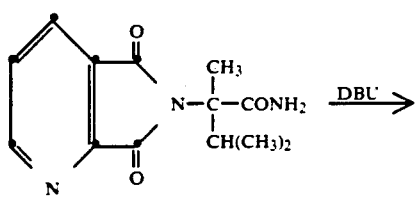

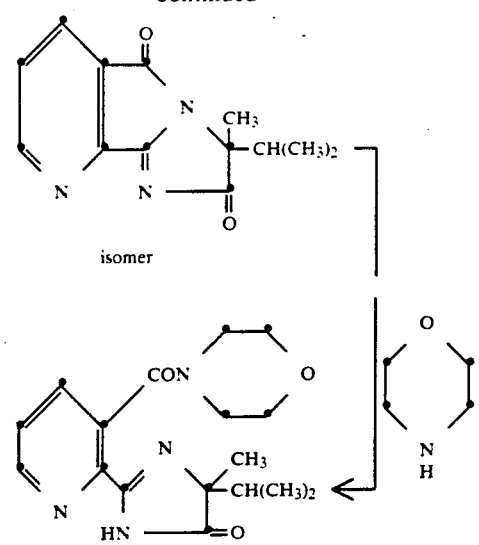

The cyclization of the amide is accomplished by heating 7.83 g of amide in 150 ml of toluene and 0.45 ml of 1,8-diazabicyclo[5,4,0]undec-7-ene under a Dean-Stark water Separator for 2 hours as described in Example 4. The separator is removed. 4 ml of morpholine is added and heating continued for 3 hours. The mixture is concentrated and the residue chromatographed on silica gel in ethyl acetate. The product is eluted first and this material is recrystallized from ether-hexane to give pure amide mp 143°-145.5° C.

By substituting the appropriate amine for morpholine, the following amides are prepared.

| $R_6$ | mp °C. |
|---|---|
| —$CH_2C\equiv CH$ | 171-173.5 |
| ⌬—Cl | 227.5-228.5 |
| —$CH_2CH_2OH$ | 174.5-175.5 |

EXAMPLE 6

Preparation of 2-Isopropyl-2-methyl-5H-imidazo[1',2':1,2]pyrrolo[3,4-b]pyridine-3(2H),5-dione

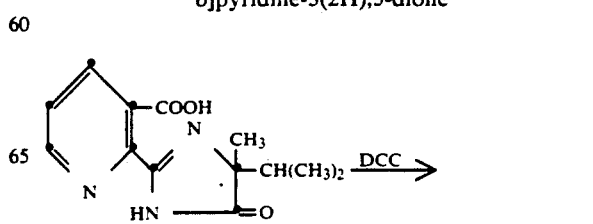

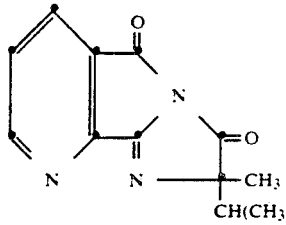

To a solution containing 50.9 g of dicyclohexylcarbodiimide in 600 ml of dry methylene chloride is added, while stirring, 60 g of the acid at such a rate that the temperature does not exceed 32° C. After stirring at room temperature for 2.5 hours, the mixture is filtered and the filtrate concentrated to give a white solid. This solid is recrystallized from methylene chloride to give 57.4 g of the dione, mp 125°–128.5° C. The analytically pure dione melts at 132°–134° C.

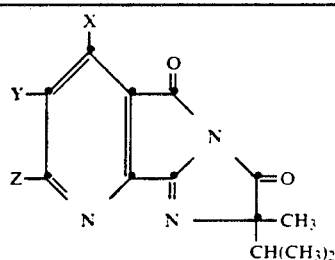

| X | Y | Z | mp °C. |
|---|---|---|---|
| H | H | $C_3H_7$ | 98.5–101 |
| H | H | $CH(CH_3)_2$ | 100–105 |
| H | $CH(CH_3)_2$ | H | 128–137 |
| H | $C_2H_5$ | H | 126–131 |
| H | H | $C_2H_5$ | 148–152.5 |
| H | $OCH(CH_3)_2$ | H | 157–161 |

EXAMPLE 7

Preparation of the Acetone oxime ester of 2-(5-isopropyl-5-methyl-4-oxo-2-imidazolin-2-yl)nicotinic acid

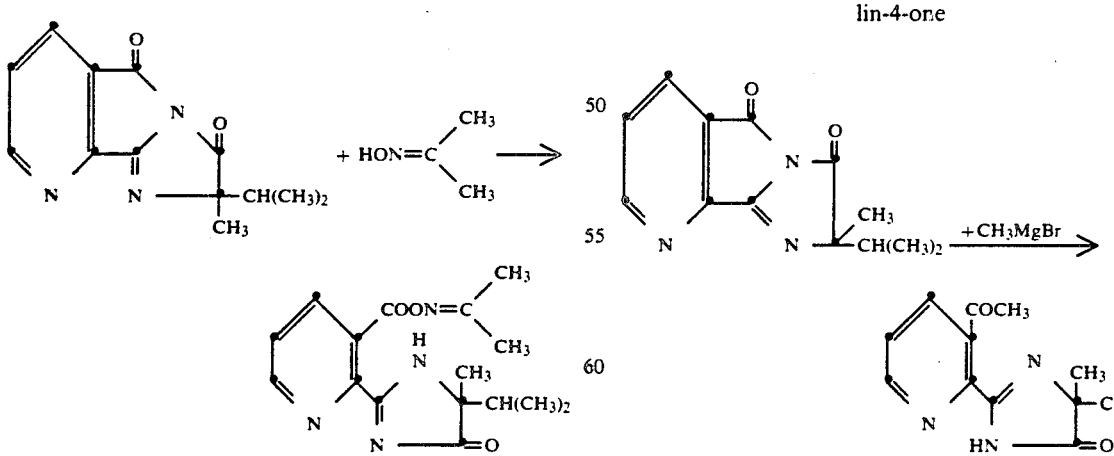

To a solution containing 2.0 g of the 3,5-dione in 15 ml of toluene is added 0.6 g of acetone oxime. The mixture is heated and stirred at 50°–60° C. for 2.75 hours. After stirring overnight at room temperature, the solvent is removed and the residue chromatographed on silica gel using 10% acetonitrile in methylene chloride followed by 30% acetonitrile in methylene chloride as the eluent. Toluene is removed from the fractions containing the product and the product collected. This is recrystallized from methylene chloride-hexane to give analytically pure oxime ester mp 117°–119.5° C. The ester from 2,2,2-trichloroethanol mp 114°–116° C. is prepared in essentially the same manner. Other esters prepared in the same manner are listed below.

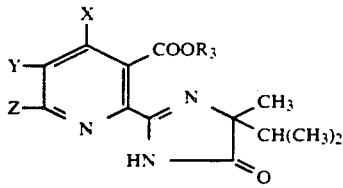

| $R_3$ | X | Y | Z | mp °C. |
|---|---|---|---|---|
| $CH_3$ | H | $C_2H_5$ | H | 96–99 |
| $CH(CH_3)_2$ | H | $C_2H_5$ | H | 106–108 |
| $CH_2C\equiv CH$ | H | $C_2H_5$ | H | 143–145 |
| $CH_2C_6H_5$ | H | $C_2H_5$ | H | 121–123.5 |
| $C_2H_5$ | H | $C_2H_5$ | H | 84.5–86.5 |
| $CH_2\text{-furyl}$ | H | $C_2H_5$ | H | gum |
| $CH_3$ | H | $OCH(CH_3)_2$ | H | gum |
| $C_2H_5$ | H | $OCH(CH_3)_2$ | H | 96–101 |
| $CH_2C\equiv CH$ | H | $OCH(CH_3)_2$ | H | 124–125 |
| $CH(CH_3)_2$ | H | $OCH(CH_3)_2$ | H | 95–99 |
| $CH_2\text{-furyl}$ | H | $OCH(CH_3)_2$ | H | 123–125 |
| $CH_2-C_6H_5$ | H | $OCH(CH_3)_2$ | H | 145–146.5 |
| $CH_3$ | H | OH | H | 200.5–202 |

EXAMPLE 8

Preparation of 2-(3-Acetyl-2-pyridyl)-5-isopropyl-5-methyl-2-imidazolin-4-one

To a stirred solution containing 10.0 g of the dione in 100 ml of dry tetrahydrofuran under nitrogen and −78° C. is added dropwise 15.1 ml of a 3M solution of methyl magnesium bromide in ether. A temperature of < −60°

C. is maintained during the addition. After the addition, stirring is continued at −78° C. and then the mixture warmed slowly to room temperature. The mixture is diluted with an equal volume of water, the pH adjusted to 4 with glacial acetic acid and extracted three times with methylene chloride. The combined extracts are dried and concentrated. The residue is chromatographed on silica gel with ether. Concentration of the appropriate fractions give 6.1 g of product as a crystalline solid mp 104°–108° C. An analytically pure sample has mp 103°–105° C.

Using essentially the same procedure as described above but substituting phenyl lithium or sodium trimethyl phosphonoacetate for methyl magnesium bromide, the following imidazolinones are prepared.

| A | mp °C. |
|---|---|
| COC₆H₅ | 138–140.5 |
| CO—CH(COOCH₃)(P(OCH₃)₂=O) | 131.5–134 |

EXAMPLE 9

Preparation of 2-[3-(Hydroxymethyl)-2-pyridyl]-5-isopropyl-5-methyl-2-imidazolin-4-one

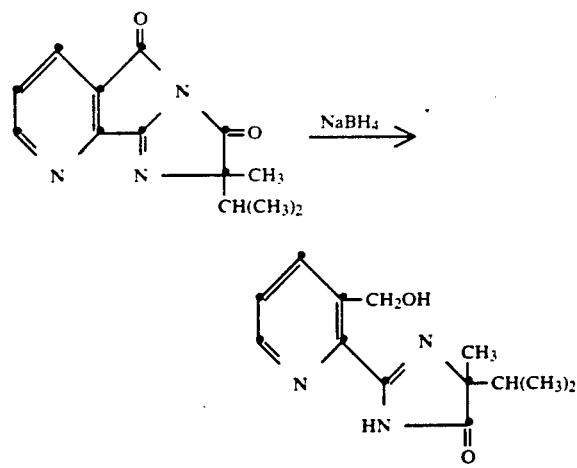

To a stirred solution of 0.32 g sodium borohydride in 25 ml absolute ethanol at 0° C. is added during 10 minutes with stirring a solution containing 2.0 g dione in 25 ml dry tetrahydrofuran. The mixture is then stirred a further three hours at room temperature. The mixture is poured into 200 ml ice water, extracted with methylene chloride, the extract dried and concentrated. The residue is crystallized from methylene-chloride-hexane to give the desired product. The analytically pure sample has mp 145°–149° C.

EXAMPLE 10

Preparation of Ethyl-2-(5-isopropyl-5-methyl-4-oxo-2-imidazolin-2-yl)-3-quinolinecarboxylic acid Procedure A

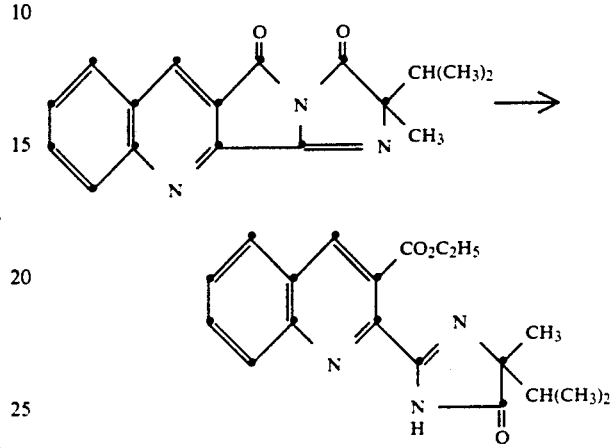

To 2-isopropyl-2-methyl-5-H-imidazo[1′, 2′:1,2] pyrazolo [3,4-b]quinoline-3H(2H),5-dione (2 g, 0.0068 mol) in absolute ethanol (40 ml) under nitrogen is added 50% sodium hydride (0.34 g, 0.00716 mol) with ice-cooling. Gas evolution is observed. After 10 minutes the reaction is neutralized with aqueous ammonium chloride, stripped and partitioned between water and ethyl acetate. The organic layer is separated and dried over anhydrous magnesium sulfate, filtered, stripped and the residue crystallized from ethyl acetate-hexane to give 1.38 g (60%) of a white solid, mp 146°–147.5° C.

In a similar manner, the following esters in Table IV may be prepared by Procedure A.

EXAMPLE 11

Preparation of Methyl-2-(5-isopropyl-5-methyl-4-oxo-2-imidazolin-2-yl)-3-quinolinecarboxylic acid Procedure B

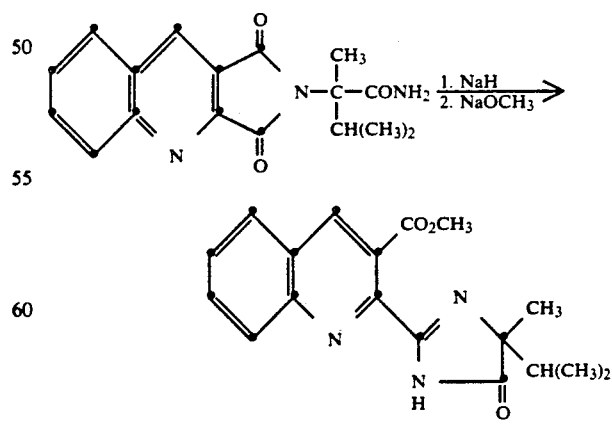

A 50% sodium hydride oil dispersion (1.4 g, 0.0292 mol) is added to azeotropically dried 1,3-dihydro-α-isopropyl-α-methyl-1,3-dioxo-2-H-pyrrolo [3,4-b]quinoline-2-acetamide (6 g, 0.0193 mol) in xylene, under nitrogen. The mixture is heated and stirred under reflux for six hours, cooled and slowly quenched with a solution of sodium methoxide (0.1 g) in methanol (20 ml). After heating at 60° C. for 3 hours the mixture is filtered and the filtrate stripped to give a white solid, which is dissolved in a methylene chloride-water mixture. Separation of the organic layer and stripping afforded a solid of 0.48 g, which is purified by passing through a silica gel pad with ethyl acetate as solvent. After removal of the solvent, the solid residue is crystallized from ethyl acetate-hexane to give white needles of the required ester, 0.4 g, mp 145°-154° C. Anal. calcd. for $C_{18}H_{19}N_3O_3$: C, 66.44; H, 5.89; N, 12.92. Found: C, 66.35; H, 5.93; N, 12.83.

EXAMPLE 12

Preparation of 2-isopropyl-2-methyl-5H-imidazo[1',2':1,2]-pyrrolo[3,4b]quinoline-3(2H),5-dione Procedure A

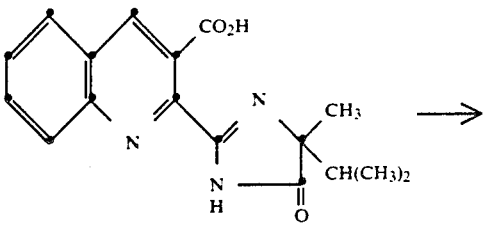

TABLE IV

| $R_3$ | $R_1$ | $R_2$ | X | L | M | Q | $R_7$ | mp °C. | Example Procedure |
|---|---|---|---|---|---|---|---|---|---|
| $CH_3$ | $CH_3$ | $CH(CH_3)_2$ | H | H | H | H | H | 145–154 | B |
| $C_2H_5$ | $CH_3$ | $CH(CH_3)_2$ | H | H | H | H | H | 146–147.5 | A |
| $CH(CH_3)_2$ | $CH_3$ | $CH(CH_3)_2$ | H | H | H | H | H | | |
| $CH_2CH=CH_2$ | $CH_3$ | $CH(CH_3)_2$ | H | H | H | H | H | | |
| $CH_2$-(methylenedioxy) | $CH_3$ | $CH(CH_3)_2$ | H | H | H | H | H | 163–165.5 | A |
| $CH_2C_6H_5$ | $CH_3$ | $CH(CH_3)_2$ | H | H | H | H | H | 159–161 | A |
| $C_6H_5$ | $CH_3$ | $CH(CH_3)_2$ | H | H | H | H | H | | |
| $C_8H_{17}$ | $CH_3$ | $CH(CH_3)_2$ | H | H | H | H | H | | A |
| $CH_3$ | $CH_3$ | $C_2H_5$ | H | H | H | H | H | | |
| $CH_2$-(methylenedioxy) | $CH_3$ | $C_2H_5$ | H | H | H | H | H | | A |
| $CH_3$ | $CH_3$ | $CH(CH_3)_2$ | H | H | $CH_3$ | H | H | | |
| $CH_3$ | $CH_3$ | $CH(CH_3)_2$ | H | H | H | Cl | H | | |
| $CH_3$ | $CH_3$ | $CH(CH_3)_2$ | H | H | $N(CH_3)_2$ | H | H | 63–66 | |
| $C_4H_9$ | $CH_3$ | $CH(CH_3)_2$ | H | H | H | H | H | 133.5–134.5 | A |
| $CH_3$ | $CH_3$ | $C_2H_5$ | H | H | H | H | H | | |
| $CH_3$ | $CH_3$ | cyclopropyl | H | H | H | H | H | | |
| $CH_3$ | $CH_3$ | sec-$C_4H_9$ | H | H | H | H | H | | |
| $CH_3$ | —$(CH_2)_5$— | | H | H | H | H | H | | |
| $CH_3$ | $CH_3$ | $CH(CH_3)_2$ | H | H | H | $CH_3$ | H | 150–165 | |
| $CH_3$ | $CH_3$ | $CH(CH_3)_2$ | H | H | H | H | $NO_2$ | 243–245 | |
| $CH_3$ | $CH_3$ | $CH(CH_3)_2$ | H | H | H | H | $NH_2$ | 231–233 | |
| $CH_3$ | $CH_3$ | $CH(CH_3)_2$ | H | H | H | H | $N(CH_3)_2$ | 149–152 | |
| $CH_3$ | $CH_3$ | $CH(CH_3)_2$ | H | H | $NO_2$ | H | H | 206–208 | |
| $CH_3$ | $CH_3$ | $CH(CH_3)_2$ | H | H | $NO_2$ | H | H | 193–194.5 | |
| $CH_3$ | $CH_3$ | $CH(CH_3)_2$ | H | H | $NHCOCH_3$ | H | H | 239–240 | |

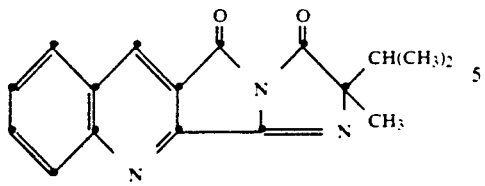

Dicyclohexylcarbodiimide (3.47 g, 0.0168 mol) in methylene chloride under nitrogen is added to a stirred suspension of 2-(5-isopropyl-5-methyl-4-oxo-2-imidazolin-2-yl)-3-quinolinecarboxylic acid, (5.24 g, 0.0168 mol) in methylene chloride at room temperature overnight. Since reaction was incomplete a further 0.3 g of dicyclohexylcarbodiimide was added and the mixture stirred for a further 48 hours. The reaction mixture is evaporated to a yellow solid and is purified by chromatography on a silica gel column. The product elutes with acetonitrile-methylene chloride as a white solid, which is crystallized from toluene as mp 225°–227° C. Anal. calcd. for $C_{17}H_{15}N_3O_2$: C, 69.61; H, 5.15; N, 14.33. Found: C, 69.76, H, 5.31; N, 14.13.

EXAMPLE 13

Procedure B

Preparation of cis and trans 1,11b-Dihydro-11b-hydroxy-3-isopropyl-3-methyl-5-H-imidazo[1',2':1,2]pyrrolo [3,4-b]quinoline-2(3H),5-dione

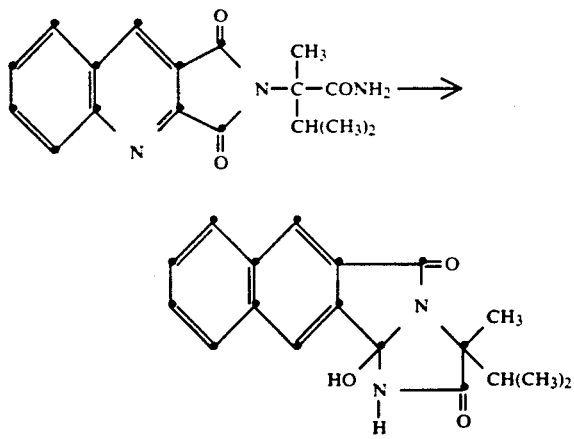

A solution of 1,3-dihydro-α-isopropyl-α-methyl-1,3-dioxo-2-H-pyrrolo[3,4-b]quinoline-2-acetamide (0.5 g, 0.0016 mol) was heated under reflux in xylene for 23 hours. On cooling, a white solid 0.17 g, mp 191°–192° C. precipitates and a further crop of 0.1 g, mp 187°–189° C. is formed by dilution of the filtrate by hexane. Anal. calcd. for $C_{17}H_{17}N_3O_3$: C, 65.58; H, 5.50; N, 13.50. Found: C, 66.08; H, 5.65; N, 13.00.

Other tricycles are obtained by procedures similar to Procedures A and B above.

Examples of Tricycles:

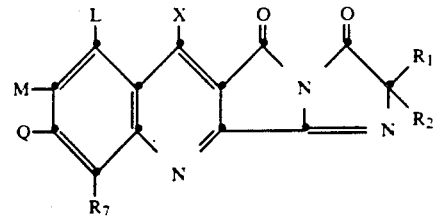

| | | | |
|---|---|---|---|
| Q = CH₃ | X.L.M.R₇ = H | R₁ = CH₃ | R₂ = CH(CH₃)₂ |
| Q = Cl | X.L.M.R₇ = H | R₁ = CH₃ | R₂ = CH(CH₃)₂ |
| M = CH₃ | X.L.Q.R₇ = H | R₁ = CH₃ | R₂ = CH(CH₃)₂ |
| M = Cl | X.L.Q.R₇ = H | R₁ = CH₃ | R₂ = CH(CH₃)₂ |
| Q = CF₃ | X.L.M.R₇ = H | R₁ = CH₃ | R₂ = CH(CH₃)₂ |
| M = N(CH₃)₂ | X.L.Q.R₇ = H | R₁ = CH₃ | R₂ = CH(CH₃)₂ |
| M = OCH₃ | X.L.Q.R₇ = H | R₁ = CH₃ | R₂ = CH(CH₃)₂ |
| X = OH | L.M.Q.R₇ = H | R₁ = CH₃ | R₂ = CH(CH₃)₂ |

| X.L.M.R.Q = H | R₁ | R₂ |
|---|---|---|
| | CH₃ | C₂H₅ |
| | CH₃ | C₃H₇ |
| | CH₃ | C₄H₉-n |
| | CH₃ | C₄H₉-sec |
| | CH₃ | C₄H₉-iso |
| | CH₃ | 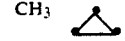 |
| | —(CH₂)₅— | |
| | CH₃ | 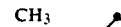 |

I claim:
1. A process for the preparation of a compound having the structure:

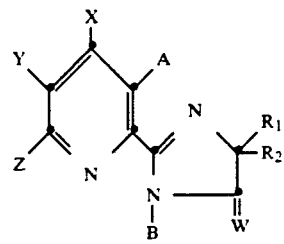

wherein
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
A is $COOR_3$ or $CONHR_6$;
$R_3$ is
  $C_1$–$C_{12}$ alkyl optionally substituted with one of the following groups: $C_1$–$C_3$ alkoxy, halogen, hydroxyl, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;
  $C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups:

$C_3$–$C_6$ cycloalkyl optionally substituted with one or two $C_1$–$C_3$ alkyl groups;

$C_3$–$C_{10}$ alkynyl optionally substituted with one or two $C_1$–$C_3$ alkyl groups; or, A cation of alkali metals, alkaline earth metals, manganese, copper, iron, zinc, cobalt, lead, silver, nickel, ammonium or organic ammonium;

$R_6$ is hydrogen, hydroxyl, $C_3$-alkenyl, $C_3$-alkynyl or $C_1$–$C_4$ alkyl optionally substituted with one hydroxyl or one chlorine group;

B is H;

W is O;

X is hydrogen, halogen, hydroxyl or methyl, with the proviso that when Y and Z are taken together to form a ring and YZ is represented by the structure; —(CH$_2$)$_n$—, where n is 3 or 4, is X is hydrogen;

Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen; and, when taken together, Y and Z may form a ring in which YZ are represented by the structure: —(CH$_2$)$_n$—, where n is an integer of 3 or 4, provided that X is hydrogen; or

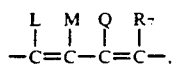

where L, M, Q and $R_7$ are each hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, NO$_2$, CN, phenyl, phenoxy, amino, $C_1$–$C_4$ alkylamino, diloweralkylamino, chlorophenyl, methylphenyl, or phenoxy substituted with one Cl, CF$_3$, NO$_2$ or CH$_3$ group, with the proviso that only one of L, M, Q or $R_7$ may represent a substituent other than hydrogen, halogen, $C_1$–$C_4$ alkyl or $C_1$–$C_4$ alkoxy;

comprising; reacting a compound having the structure:

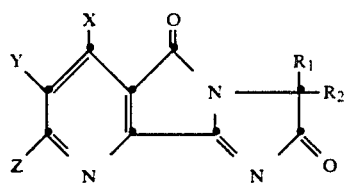

wherein $R_1$, $R_2$, X, Y and Z are as described above; with (a) at least one equivalent of an alcohol represented by the structure $R_3$OH and an alkali metal alkoxide $R_3$O$^-$M$^+$, where $R_3$ is a described above and M$^+$ is an alkali metal, at a temperature between about 20° C. and 50° C., alone or in the presence of an aprotic solvent; whereby the desired product, in which A is COOR$_3$ and $R_3$, $R_1$, $R_2$, X, Y and Z are as described above, is formed; or with (b) at least one equivalent of an amine represented by the structure $R_6$NH$_2$, where $R_6$ is as described above, alone or in the presence of an aprotic solvent, at a temperature between about 80° C. and 125° C., whereby the desired product, in which A is CONHR$_6$ and $R_6$, $R_1$, $R_2$, X, Y and Z are as described above, is formed.

2. A process for the preparation of a compound having the structure:

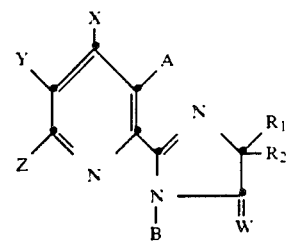

wherein $R_1$ is $C_1$–$C_4$alkyl;

$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;

A is COOR$_3$, CONHR$_6$, CH$_2$OH, COCH$_3$ COC$_6$H$_5$, or

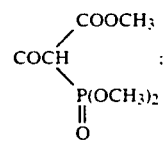

$R_3$ is diloweralkylimino $C_1$–$C_{12}$ alkyl optionally substituted with one of the following groups: $C_1$–$C_3$ alkoxy, halogen, hydroxyl, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups;

$C_3$–$C_{10}$ alkynyl optionally substituted with one or two $C_1$–$C_3$ alkyl groups; or, A cation of alkali metals, alkaline earth metals, manganese, copper, iron, zinc, cobalt, lead, silver, nickel, ammonium or aliphatic ammonium;

$R_6$ is hydrogen, hydroxyl, $C_3$-alkenyl, $C_3$-alkynyl or $C_1$–$C_4$ alkyl optionally substituted with one hydroxyl or one chlorine group;

B is H;

W is O;

X is hydrogen, halogen, hydroxyl or methyl, with the proviso that when Y and Z are taken together to form a ring and YZ is represented by the structure: —(CH$_2$)$_n$—, where n is 3 or 4, X is hydrogen;

Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen; and, when taken together, Y and Z may form a ring in which YZ are represented by the structure: —(CH$_2$)$_n$—, where n is an integer of 3 or 4, provided that X is hydrogen; or

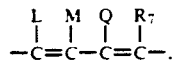

where L, M, Q and $R_7$ are each hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$, may represent a substituent other than hydrogen, halogen, $C_1$-$C_4$ alkyl or $C_1$-$C_4$-alkoxy;

comprising, reacting a compound having the structure:

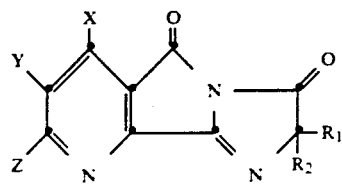

wherein $R_1$, $R_2$, X, Y and Z are as described above; with a) at least one equivalent of an alcohol represented by the structure $R_3OH$ and an alkali metal alkoxide $R_3O^{\ominus}M^-$, where $R_3$ is as described above and M is an alkali metal, alone or in the presence of an aprotic solvent at a temperature between 20° C. and 50° C., whereby the desired product, in which A is $COOR_3$ and $R_3$, $R_1$, $R_2$, X, Y and Z are as described above, is obtained;

b) at least one equivalent of an amine represented by the structure $R_6NH_2$, where $R_6$ is as described above, in the presence of a loweralkyl alcohol or an aprotic solvent at a temperature between about 80° C. and 125° C., whereby the desired product, in which A is $CONHR_6$ and $R_6$, $R_1$, $R_2$, X, Y and Z are as described above, is obtained;

c) at least one equivalent of methyl magnesium bromide, in the presence of an aprotic solvent at a temperature between −50° C. and −80° C. under a blanket of inert gas, whereby the desired product in which A is $COCH_3$ and $R_1$, $R_2$, X, Y and Z are as described above, is obtained;

d) at least one equivalent phenyl lithium, in the presence of an aprotic solvent at a temperature between −50° C. and −80° C. under a blanket of of inert gas, whereby the desired product, in which A is $COC_6H_5$ and $R_1$, $R_2$, X, Y and Z are as described above, is obtained; or e) at least one equivalent of trimethylphosphonoacetate, in the presence of an aprotic solvent at −50° C. to −80° C. under a blanket of inert gas, whereby the desired product in which A is

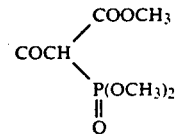

and $R_1$, $R_2$, X, Y and Z are as described above, is obtained; or f) at least one equivalent of sodium borohydride in ethanol at −10° to +20° C. whereby the desired product in which A is $CH_2OH$, is obtained.

* * * * *